United States Patent
Biafore et al.

(10) Patent No.: US 10,474,042 B2
(45) Date of Patent: Nov. 12, 2019

(54) STOCHASTICALLY-AWARE METROLOGY AND FABRICATION

(71) Applicant: KLA-Tencor Corporation, Milpitas, CA (US)

(72) Inventors: John J. Biafore, North Scituate, RI (US); Moshe E. Preil, Sunnyvale, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 15/612,279

(22) Filed: Jun. 2, 2017

(65) Prior Publication Data

US 2018/0275523 A1 Sep. 27, 2018

Related U.S. Application Data

(60) Provisional application No. 62/475,072, filed on Mar. 22, 2017.

(51) Int. Cl.
  *G03F 7/20* (2006.01)
  *G01N 21/88* (2006.01)
  (Continued)

(52) U.S. Cl.
  CPC ....... *G03F 7/7065* (2013.01); *G01N 21/8806* (2013.01); *G01N 21/8851* (2013.01);
  (Continued)

(58) Field of Classification Search
  CPC .............. G03F 7/7065; G01N 21/8806; G01N 21/95607; G01N 2021/95676
  See application file for complete search history.

(56) References Cited

U.S. PATENT DOCUMENTS 5,608,526 A 3/1997 Piwonka-Corle et al.
5,859,424 A 1/1999 Norton et al.
(Continued)

FOREIGN PATENT DOCUMENTS

KR 20150140349 A 12/2015

OTHER PUBLICATIONS

Lee, Myungjun, et al., Quantifying imaging performance bounds of extreme dipole illumination in high NA optical lithography, Photomask Technology 2016, Oct. 3, 2016, 16 pages, Proceedings vol. 9985; 99850X, San Jose, California, USA.
(Continued)

*Primary Examiner* — Deoram Persaud
(74) *Attorney, Agent, or Firm* — Suiter Swantz pc llo

(57) ABSTRACT

A system for stochastically-aware metrology includes a controller to be communicatively coupled to a fabrication tool. The controller receives a production recipe including at least a pattern of elements to be fabricated on a sample and one or more exposure parameters for exposing the pattern of elements, identifies candidate care areas of the pattern of elements susceptible to stochastic repeaters including fabrication defects predicted to occur stochastically when fabricated according to the production recipe, selects one or more care areas from the candidate care areas by comparing one or more predicted likelihoods of the one or more stochastic repeaters to a defect likelihood threshold, modifies the production recipe to mitigate the stochastic repeaters within the one or more care areas within a selected tolerance, and directs the fabrication tool to fabricate at least one sample according to the modified production recipe.

36 Claims, 8 Drawing Sheets

(51) Int. Cl.
 *G05B 23/02* (2006.01)
 *G01N 21/956* (2006.01)
(52) U.S. Cl.
 CPC ..... *G01N 21/956* (2013.01); *G01N 21/95607* (2013.01); *G05B 23/0254* (2013.01); *G01N 2021/8883* (2013.01); *G01N 2021/95676* (2013.01); *G05B 23/0294* (2013.01)

(56) References Cited

U.S. PATENT DOCUMENTS

| | | | |
|---|---|---|---|
| 6,429,943 | B1 | 8/2002 | Opsal |
| 7,478,019 | B2 | 1/2009 | Zangooie et al. |
| 2008/0279445 | A1 | 11/2008 | Matsui et al. |
| 2009/0206252 | A1* | 8/2009 | Okazaki ................ G06T 7/0006 250/307 |
| 2012/0029858 | A1 | 2/2012 | Kulkarni et al. |
| 2012/0278768 | A1* | 11/2012 | Yang ................... G03F 7/70125 716/52 |
| 2013/0031518 | A1* | 1/2013 | Robles ............... G06F 17/5081 716/52 |
| 2013/0176558 | A1* | 7/2013 | Lin ....................... G01B 11/24 356/237.5 |
| 2013/0252350 | A1 | 9/2013 | Lee et al. |
| 2014/0172394 | A1* | 6/2014 | Kuznetsov .......... G06F 17/5009 703/6 |
| 2014/0297211 | A1* | 10/2014 | Pandev ............... G03F 7/70558 702/81 |
| 2014/0316730 | A1* | 10/2014 | Shchegrov ............ H01L 22/12 702/81 |
| 2015/0042984 | A1* | 2/2015 | Pandev ............... G03F 7/70641 356/124 |
| 2015/0046118 | A1* | 2/2015 | Pandev .................. H01L 22/12 702/155 |
| 2015/0168851 | A1* | 6/2015 | Li ............................ G03F 1/36 355/55 |
| 2016/0377561 | A1 | 12/2016 | Ramachandran et al. |
| 2017/0010538 | A1* | 1/2017 | Hansen .................. G03F 7/705 |
| 2017/0345725 | A1* | 11/2017 | Hu .......................... H01L 22/12 |
| 2018/0011407 | A1* | 1/2018 | Hsu .................... G03F 7/70433 |

OTHER PUBLICATIONS

International Search Report and Written Opinion dated Jul. 2, 2018 for PCT/US2018/022769.

* cited by examiner

STOCHASTICALLY-AWARE METROLOGY AND FABRICATION

CROSS-REFERENCE TO RELATED APPLICATION

The present application claims the benefit under 35 U.S.C. § 119(e) of U.S. Provisional Application Ser. No. 62/475,072, filed Mar. 22, 2017, entitled STOCHASTICALLY AWARE METROLOGY AND INSPECTION, naming John J. Biafore and Moshe E. Preil as inventors, which is incorporated herein by reference in the entirety.

TECHNICAL FIELD

The present invention relates generally to metrology systems and, more particularly, to stochastically-aware metrology systems.

BACKGROUND

Illumination sources with decreasing wavelength may be utilized to meet demands for ever-shrinking features on semiconductor devices. However, decreasing the wavelength of illumination sources in lithography systems may increase the occurrence of defects that occur randomly or with a certain probability during fabrication, particularly in high-volume manufacturing in which exposure dose is minimized to increase throughput and decrease fabrication costs. Accordingly, the number and location of defects generated during a given fabrication run may vary. This increased likelihood of stochastic defects with short-wavelength illumination sources may be associated with a variety of factors including increased photon energy coupled with a reduced number of photons incident on a sample as well as stochastic variations in the absorption of these photons.

The presence of stochastic defects that manifest randomly (e.g. stochastic repeaters) provides increased challenges for defect detection as well as the generation of sample layouts and production recipes designed to mitigate the impact of these stochastic repeaters.

SUMMARY

A system is disclosed in accordance with one or more illustrative embodiments of the present disclosure. In one illustrative embodiment, the system includes a controller to be communicatively coupled to a fabrication tool. In another illustrative embodiment, the controller receives a production recipe including at least a pattern of elements to be fabricated on a sample and one or more exposure parameters for exposing the pattern of elements with illumination during fabrication of the sample. In another illustrative embodiment, the controller identifies one or more candidate care areas of the pattern of elements susceptible to one or more stochastic repeaters when fabricated according to the production recipe. In another illustrative embodiment, the one or more stochastic repeaters include one or more fabrication defects predicted to occur stochastically when fabricated according to the production recipe. In another illustrative embodiment, the controller selects one or more care areas from the one or more candidate care areas by comparing one or more predicted likelihoods of the one or more stochastic repeaters to a defect likelihood threshold. In another illustrative embodiment, the controller modifies the production recipe to mitigate the one or more stochastic repeaters within the one or more care areas within a selected tolerance. In another illustrative embodiment, the controller directs the fabrication tool to fabricate at least one sample according to the modified production recipe.

A method is disclosed in accordance with one or more illustrative embodiments of the present disclosure. In one illustrative embodiment, the method includes receiving a production recipe including at least a pattern of elements to be fabricated on a sample and one or more exposure parameters for exposing the pattern of elements with illumination. In another illustrative embodiment, the method includes identifying one or more candidate care areas of the pattern of elements susceptible to stochastic repeaters when fabricated according to the production recipe. In another illustrative embodiment, the one or more stochastic repeaters include one or more fabrication defects predicted to occur stochastically when fabricated according to the production recipe. In another illustrative embodiment, the method includes selecting one or more care areas from the one or more candidate care areas by comparing one or more predicted likelihoods of one or more stochastic repeaters to a defect likelihood threshold. In another illustrative embodiment, the method includes modifying the production recipe to mitigate predicted occurrences of the one or more stochastic repeaters within the one or more care areas within a selected tolerance. In another illustrative embodiment, the method includes fabricating at least one sample according to the modified production recipe.

A system is disclosed in accordance with one or more illustrative embodiments of the present disclosure. In one illustrative embodiment, the system includes a controller to communicatively couple to a metrology tool and a fabrication tool. In one illustrative embodiment, the controller receives a production recipe including at least a pattern of elements to be fabricated on a sample and one or more exposure parameters for exposing the pattern of elements with illumination during fabrication of the sample. In another illustrative embodiment, the controller identifies one or more candidate care areas of the pattern of elements susceptible to one or more stochastic repeaters when fabricated according to the production recipe. In another illustrative embodiment, the one or more stochastic repeaters include one or more fabrication defects predicted to occur stochastically when fabricated according to the production recipe. In another illustrative embodiment, the controller selects one or more care areas from the one or more candidate care areas by comparing one or more predicted likelihoods of the one or more stochastic repeaters to a defect likelihood threshold. In another illustrative embodiment, the controller directs the fabrication tool to fabricate at least one sample according to the production recipe. In another illustrative embodiment, the controller generates a metrology recipe of the metrology tool to monitor the one or more care areas. In another illustrative embodiment, the controller directs the metrology tool to inspect the one or more care areas on the at least one sample fabricated according to the production recipe.

A method is disclosed in accordance with one or more illustrative embodiments of the present disclosure. In one illustrative embodiment, the method includes receiving a production recipe including at least a pattern of elements to be fabricated on a sample and one or more exposure parameters for exposing the pattern of elements with illumination during fabrication of the sample. In another illustrative embodiment, the method includes identifying one or more candidate care areas of the pattern of elements susceptible to one or more stochastic repeaters when fabricated according to the production recipe. In another illustrative embodiment, the one or more stochastic repeaters include one or more fabrication defects predicted to occur stochastically when fabricated according to the production recipe. In another illustrative embodiment, the method includes selecting one or more care areas from the one or more candidate care areas by comparing one or more predicted likelihoods of the one or more stochastic repeaters to a defect likelihood threshold. In another illustrative embodiment, the method includes fabricating at least one sample according to the production recipe. In another illustrative embodiment, the method includes generating a metrology recipe of a metrology tool to monitor the one or more care areas. In another illustrative embodiment, the method includes inspecting the one or more care areas on the at least one sample fabricated according to the production recipe.

It is to be understood that both the foregoing general description and the following detailed description are exemplary and explanatory only and are not necessarily restrictive of the invention as claimed. The accompanying drawings, which are incorporated in and constitute a part of the specification, illustrate embodiments of the invention and together with the general description, serve to explain the principles of the invention.

BRIEF DESCRIPTION OF DRAWINGS

The numerous advantages of the disclosure may be better understood by those skilled in the art by reference to the accompanying figures in which.

DETAILED DESCRIPTION

Figure 1A:
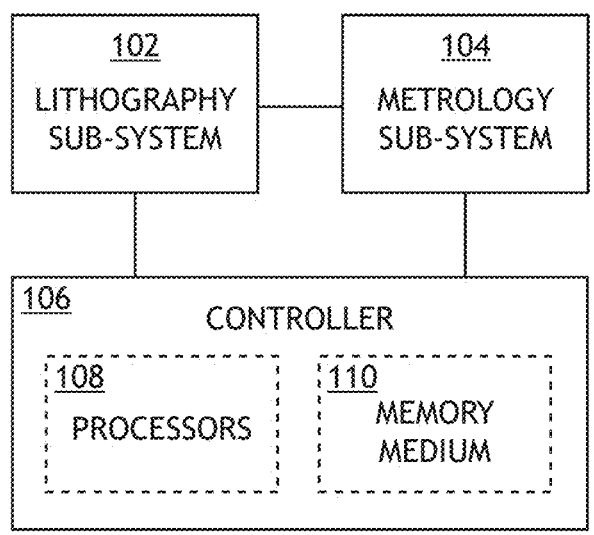
FIG. 1A is a conceptual view illustrating a semiconductor device system, in accordance with one or more embodiments of the present disclosure.

Reference will now be made in detail to the subject matter disclosed, which is illustrated in the accompanying drawings. The present disclosure has been particularly shown and described with respect to certain embodiments and specific features thereof. The embodiments set forth herein are taken to be illustrative rather than limiting. It should be readily apparent to those of ordinary skill in the art that various changes and modifications in form and detail may be made without departing from the spirit and scope of the disclosure.

Embodiments of the present disclosure are directed to systems and methods for stochastically-aware fabrication and metrology. A semiconductor device may be formed as multiple layers of printed elements fabricated through a series of additive or subtractive process steps such as, but not limited to, one or more material deposition steps, one or more lithography steps, one or more etching steps, or one or more lift-off steps. For example, a lithography-etch (LE) process for printing features may include, but is not limited to, depositing a layer of a photosensitive material (e.g. a resist layer) onto a sample, exposing the sample with an image of a pattern mask (e.g. a reticle) to modify the resistivity of the photosensitive material to an etchant, and etching away either the exposed or unexposed portions of the resist to leave behind printed features corresponding to the image of the pattern mask. Further, the resist may serve as a hard mask such that an etching step may include etching past the resist into one or more layers of the sample below the photosensitive material. The resist may then optionally be removed by subsequent process steps.

The resolution of a lithography system and thus the size of features of a pattern mask that may be exposed on a sample in a single exposure step generally scales with the wavelength of light. One approach to meeting demand for decreasing feature sizes of semiconductor devices is to decrease the wavelength of the illumination source. For example, extreme ultraviolet lithography (EUVL) systems utilize extreme ultraviolet wavelengths of radiation to fabricate features with dimensions less than 10 nm. However, decreasing the wavelength of illumination during lithography to fabricate small features may increase the likelihood of stochastic fabrication defects that occur randomly or for a percentage of fabrication runs, particularly for high-volume manufacturing in which the dose of radiation exposed on the sample is minimized to provide high throughput and reduced cost while maintaining fabrication tolerances.

In particular, decreasing the wavelength of illumination during lithography decreases the number of photons from the illumination source needed to expose the sample with a given dose of radiation due to increased photon energy (e.g. the photon energy of illumination is inversely proportional to wavelength or proportional to frequency). Decreasing the number of photons incident on the sample may increase the photon shot noise (PSN), a naturally-occurring phenomenon related to the uncertainty of absorption of a photon in a given volume of a sample. As the size of features to be fabricated approaches the size of photosensitive molecules in a resist (e.g. photoacid generators (PAGs)), a random distribution of photosensitive molecules in the resist may introduce additional uncertainty associated with the absorption of photons in a given volume of the sample. Accordingly, stochastic noise associated with photon absorption may be a complex convolution of the photon statistics and the resist interaction terms. As a result, certain fabrication defects may occur stochastically, even under nominally identical fabrication conditions. Stochastically-occurring fabrication defects, or stochastic repeaters, may thus occur with a certain probability when nominally identical structures are fabricated under nominally identical conditions such as, but not limited to, at multiple locations within a field, at a given location across multiple fields on a single wafer, or at a given location on a sample across multiple wafers.

Stochastic repeaters may present multiple challenges in a fabrication environment. Typically, defects may be assumed to be deterministic such that a known defect will consistently be present when fabricated according to a known production recipe including a pattern of elements to be fabricated on a sample and exposure parameters. For example, process window qualification (PWQ) typically identifies process-limiting defects that always occur when exposure conditions fall outside of a process window. For instance, a process window may define limits on the defocus associated with the position of the sample along the optical axis of the lithography tool (e.g. the focal position of the sample) or the dose of energy from the illumination source incident on the sample during exposure. Accordingly, the presence of stochastic repeaters that do not always occur under given exposure conditions may introduce uncertainty into typical PWQ algorithms.

Embodiments of the present disclosure are directed to determining a probability that a particular stochastic repeater may occur (e.g. a percentage of times for which the stochastic repeater is expected to occur within a field, across multiple fields on a wafer, across multiple wafers, or the like) when fabricated according to a production recipe. For example, one or more care areas including stochastic repeaters may be identified.

Additional embodiments are directed to modifying the production recipe (e.g. the design of the pattern of elements, the exposure conditions, or the like) to mitigate the fabrication of the stochastic defects. For example, modifying the production recipe may include modifying exposure conditions such as, but not limited to, the dose of illumination or the location of the wafer in the focal volume of a lithography tool during an exposure step. By way of an additional example, modifying the production recipe may include modifying the design of pattern elements to be fabricated to mitigate the occurrence of stochastic repeaters.

Additional embodiments are directed to stochastically-aware metrology. In the present disclosure, "metrology" may refer to any type of measurement of features on a sample (e.g. a wafer, a pattern mask, or the like). For example, metrology may include one or measurements to characterize the size, orientation, or distribution of elements on a surface (e.g. critical dimension metrology, or the like). By way of another example, metrology may include measurements of the positions of features fabricated on a sample in different steps to determine relative positions of fabricated sample layers (e.g. overlay metrology, or the like). By way of another example, metrology may include the detection and/or identification of features of interest such as, but not limited to, defects on a sample (e.g. inspection metrology). Accordingly, in the present disclosure, the terms "metrology" and "inspection" may be used interchangeably.

Additional embodiments are directed to generating metrology recipes to monitor the identified care areas that include stochastic repeaters. It is recognized herein that metrology recipes may include sampling plans providing a series of locations on a sample susceptible to defects to inspect with a metrology system. However, classifying defects merely as either "random" or "systematic" based on absolute (e.g. deterministic) repeatability may provide insufficient monitoring of the stochastic repeaters. Further embodiments are directed to determining metrology recipes suitable for inspecting samples having stochastic repeaters. For example, sample recipes may be generated to monitor stochastic repeaters based on predicted occurrences (e.g. as a function of location within a field, across multiple fields, across multiple wafers, or the like).

Additional embodiments are directed to selecting care areas including stochastic repeaters at least in part using stochastic simulations of the lithography process. In one instance, care areas may be selected directly by simulating lithography with one or more production recipes including sample layouts and/or exposure conditions. In another instance, a library of device patterns with predicted probabilities of stochastic defects may be generated. Accordingly, care areas of a new sample design may be selected by comparing the new sample design with the library. Further embodiments are directed to selecting care areas including stochastic repeaters at least in part by inspecting fabricated samples (e.g. pattern masks and/or wafers).

Additional embodiments are directed to selecting care areas including stochastic repeaters at least in part using additional process data. For example, contamination of either side of a wafer and/or wafer imperfections (e.g. scratches or thickness variations) may lead to "hot spots" describing regions of a wafer that may be susceptible to stochastic repeaters. In one instance, care areas may be selected based at least in part on deviations of a wafer surface from perfect flatness (e.g. provided by a process wafer geometry (PWG) tool, or the like) that may influence the focal position within a lithography tool and thus the photon density during exposure. By way of another example, electrical test data (e.g. from a wafer electrical test (WET) tool, or the like) may provide portions of a wafer that may stochastically fail an electrical test and thus provide an indication of potential stochastic repeaters. Accordingly, care areas may be selected based at least in part on sample diagnostic data.

It may be beneficial to identify stochastic defects and select metrology care areas at any production step. Additional embodiments of the present disclosure are directed to identifying care areas on a pattern mask containing a pattern of elements to be exposed on a wafer. In this regard, care areas may be selected for print check applications intended to identify potential issues with the pattern mask prior to wafer fabrication. Additional embodiments are directed to identifying care areas on a wafer. For example, care areas including stochastic repeaters may be selected for after-development inspection (ADI) in which a sample is inspected after a lithography step and prior to an etch step for the removal of either exposed or unexposed material. By way of another example, care areas including stochastic repeaters may be selected for after-etch inspection (AEI) in which a sample is inspected after material removal in an etch step.

FIG. 1A is a conceptual view illustrating a semiconductor device system 100, in accordance with one or more embodiments of the present disclosure. In one embodiment, the system 100 includes a lithography sub-system 102 for lithographically printing one or more patterns (e.g. device patterns, metrology patterns, or the like) on a sample. The lithography sub-system 102 may include any lithographic printing tool known in the art. For example, the lithography sub-system 102 may include, but is not limited to, a scanner or stepper. In another embodiment, the system 100 includes a metrology sub-system 104. For example, the metrology sub-system 104 may characterize one or more printed patterns on the sample. In this regard, the metrology sub-system 104 may measure one or more occurrences of stochastic repeaters on the sample. By way of another example, the metrology sub-system 104 may characterize a pattern mask (e.g. a pattern mask including a pattern of device elements to be exposed onto a sample by the lithography sub-system 102). In this regard, the metrology sub-system 104 may measure one or more portions of the pattern of device elements that are susceptible to fabrication defects when fabricated according to a known production recipe. In a general sense, the metrology sub-system 104 may measure any metrology metric (e.g. overlay error, pattern placement error, dimensions of sample features, critical dimensions (CD), sidewall angle, or the like) using any method known in the art. In one embodiment, the metrology sub-system 104 includes an image-based metrology tool to measure metrology data based on the generation of one or more images of a sample (e.g. a wafer, a pattern mask, or the like). In another embodiment, the metrology sub-system 104 includes a scatterometry-based metrology system to measure metrology data based on the scattering (reflection, diffraction, diffuse scattering, or the like) of light from the sample (e.g. a wafer, a pattern mask, or the like).

In another embodiment, the system 100 includes a controller 106. In another embodiment, the controller 106 includes one or more processors 108 configured to execute program instructions maintained on a memory device 110. In this regard, the one or more processors 108 of controller 106 may execute any of the various process steps described throughout the present disclosure. For example, the controller 106 may simulate one or more aspects of a lithography step (e.g. a lithography step executed by the lithography sub-system 102 according to a production recipe) to identify stochastic repeaters. By way of another example, the controller 106 may analyze and/or interpret metrology data from the metrology sub-system 104 to identify stochastic repeaters.

The one or more processors 108 of a controller 106 may include any processing element known in the art. In this sense, the one or more processors 108 may include any microprocessor-type device configured to execute algorithms and/or instructions. In one embodiment, the one or more processors 108 may consist of a desktop computer, mainframe computer system, workstation, image computer, parallel processor, or any other computer system (e.g., networked computer) configured to execute a program configured to operate the system 100, as described throughout the present disclosure. It is further recognized that the term "processor" may be broadly defined to encompass any device having one or more processing elements, which execute program instructions from a non-transitory memory device 110. Further, the steps described throughout the present disclosure may be carried out by a single controller 106 or, alternatively, multiple controllers. Additionally, the controller 106 may include one or more controllers housed in a common housing or within multiple housings. In this way, any controller or combination of controllers may be separately packaged as a module suitable for integration into system 100. Further, the controller 106 may analyze data received from the detector 142 and feed the data to additional components within the metrology sub-system 104 or external to the system 100.

The memory device 110 may include any storage medium known in the art suitable for storing program instructions executable by the associated one or more processors 108. For example, the memory device 110 may include a non-transitory memory medium. By way of another example, the memory device 110 may include, but is not limited to, a read-only memory, a random access memory, a magnetic or optical memory device (e.g., disk), a magnetic tape, a solid state drive and the like. It is further noted that memory device 110 may be housed in a common controller housing with the one or more processors 108. In one embodiment, the memory device 110 may be located remotely with respect to the physical location of the one or more processors 108 and controller 106. For instance, the one or more processors 108 of controller 106 may access a remote memory (e.g., server), accessible through a network (e.g., internet, intranet and the like). Therefore, the above description should not be interpreted as a limitation on the present invention but merely an illustration.

Figure 1B:
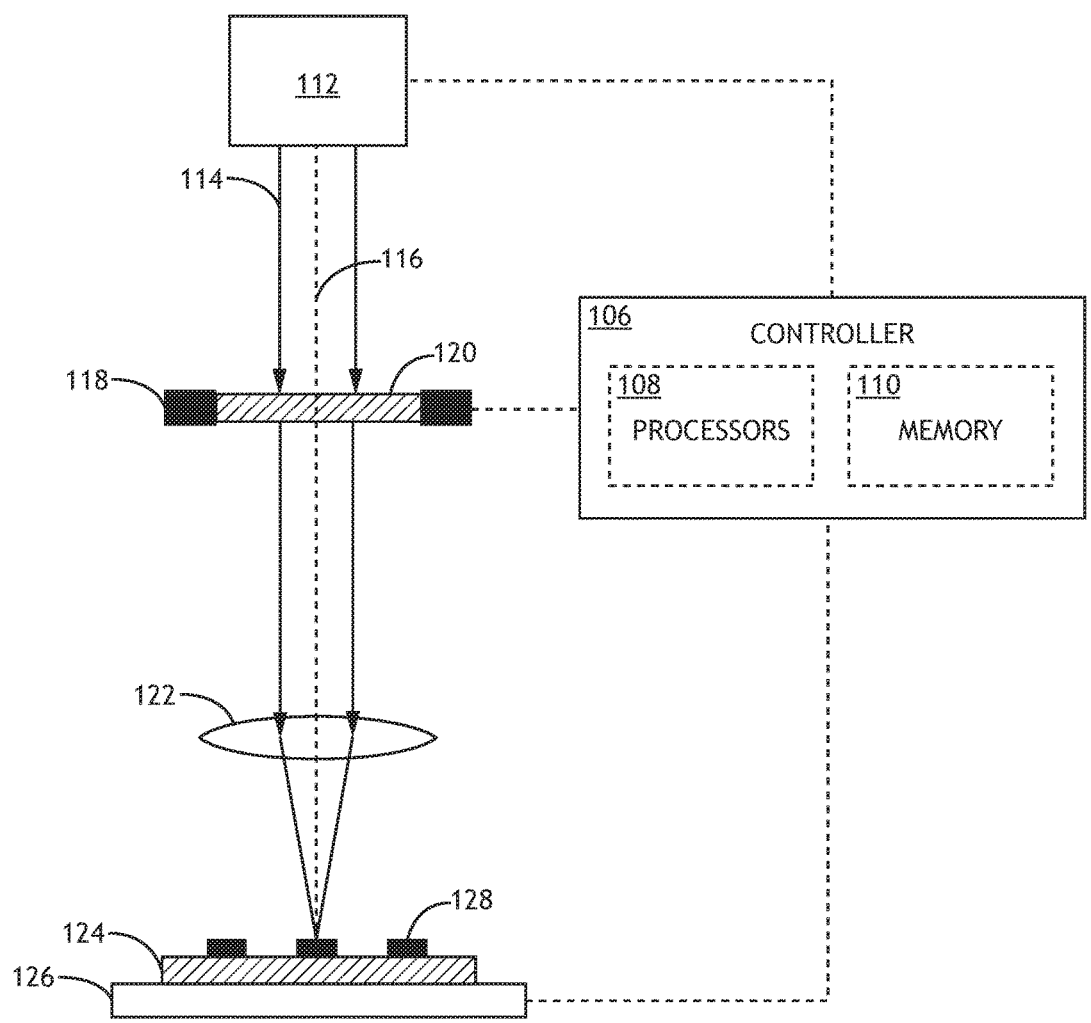
FIG. 1B is a conceptual view illustrating a lithography sub-system, in accordance with one or more embodiments of the present disclosure.

FIG. 1B is a conceptual view illustrating a lithography sub-system 102, in accordance with one or more embodiments of the present disclosure. In one embodiment, the lithography sub-system 102 includes a lithography illumination source 112 configured to generate one or more illumination beams 114. The one or more illumination beams 114 may include one or more selected wavelengths of light including, but not limited to, ultraviolet (UV) radiation, visible radiation, or infrared (IR) radiation.

The lithography illumination source 112 may include any type of illumination source known in the art suitable for generating an illumination beam 114. For example, the lithography illumination source 112 may include one or more laser systems (e.g. gas lasers, diode lasers, free-electron lasers, fiber lasers, disk lasers, for the like). By way of another example, the lithography illumination source 112 may include one or more lamp systems (e.g. arc lamps, or the like). By way of another example, the lithography illumination source 112 includes a plasma illumination source (e.g. a laser-pulsed plasma (LPP) source, a discharge pumped plasma (DPP) source, a laser-sustained plasma (LSP) source, or the like).

The lithography illumination source 112 may additionally include any number of optical elements suitable for manipulating one or more aspects of the illumination beam 114 such as, but not limited to, filters, polarizers, waveplates, or diffusers.

Illumination from the lithography illumination source 112 may have any spatial distribution (e.g. illumination pattern). For example, the lithography illumination source 112 may include, but is not limited to, a single-pole illumination source, a dipole illumination source, a C-Quad illumination source, a Quasar illumination source, or a free-form illumination source. In this regard, the lithography illumination source 112 may generate on-axis illumination beams 114 in which illumination propagates along (or parallel to) an optical axis 116 and/or any number of off-axis illumination beams 114 in which illumination propagates at an angle to the optical axis 116.

In another embodiment, the lithography sub-system 102 includes a mask support device 118. The mask support device 118 is configured to secure a pattern mask 120 including a pattern of elements to be exposed during fabrication. In another embodiment, the lithography sub-system 102 includes a set of projection optics 122 configured to project an image of the pattern mask 120 illuminated by the one or more illumination beams 114 onto a lithography sample 124 disposed on a sample stage 126 in order to generate printed pattern elements corresponding to the image of the pattern mask 120. In another embodiment, the mask support device 118 may be configured to actuate or position the pattern mask 120. For example, the mask support device 118 may actuate the pattern mask 120 to a selected position with respect to the projection optics 122 of the system 100.

As used throughout the present disclosure, the term "lithography sample" generally refers to a substrate formed of a semiconductor or non-semiconductor material (e.g. a wafer, or the like). For example, a semiconductor or non-semiconductor material may include, but is not limited to, monocrystalline silicon, gallium arsenide, and indium phosphide. For the purposes of the present disclosure, the term lithography sample and wafer should be interpreted as interchangeable.

The lithography sample 124 may include any number of photosensitive materials and/or material layers suitable for receiving the image of the pattern mask 120. For example, the lithography sample 124 may include a resist layer 128. In this regard, the set of projection optics 122 may project an image of the pattern mask 120 onto the resist layer 128 to expose the resist layer 128 and a subsequent etching step may remove the exposed material (e.g. positive etching) or the unexposed material (e.g. negative etching) in order to provide printed features on the lithography sample 124. Further, the pattern mask 120 may be utilized in any imaging configuration known in the art. For example, the pattern mask 120 may be a positive mask (e.g. a bright-field mask) in which pattern elements are positively imaged as printed pattern elements. By way of another example, the pattern mask 120 may be a negative mask (e.g. a dark-field mask) in which pattern elements of the pattern mask 120 form negative printed pattern elements (e.g. gaps, spaces, or the like).

The controller 106 may be communicatively coupled to any number of elements in the lithography sub-system 102. For example, the controller 106 may be communicatively coupled to the mask support device 118, the lithography illumination source 112, and/or the sample stage 126 to direct the exposure of pattern elements on a pattern mask 120 to a lithography sample 124 (e.g. a resist layer 128 on the sample, or the like). In this regard, exposure conditions such as the exposure dose, the focal position of the sample within the lithography sub-system 102, and the like may be adjusted.

Figure 1C:
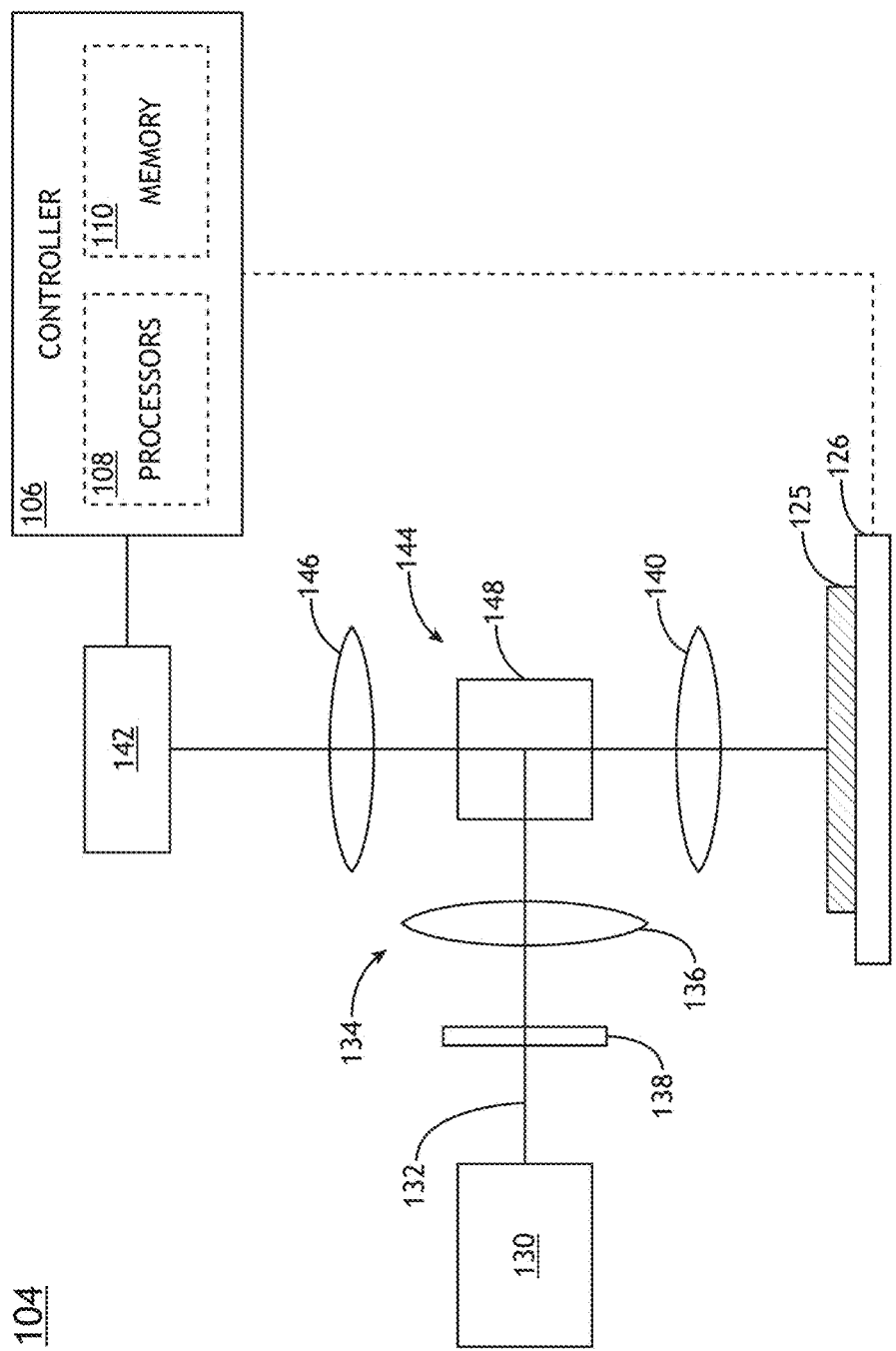
FIG. 1C is a conceptual view illustrating a metrology sub-system, in accordance with one or more embodiments of the present disclosure.

FIG. 1C is a conceptual view illustrating a metrology sub-system 104, in accordance with one or more embodiments of the present disclosure. In one embodiment, the metrology sub-system 104 includes a metrology illumination source 130 to generate a metrology illumination beam 132. In another embodiment, the metrology illumination source 130 is the same as the lithography illumination source 112. In a further embodiment, the metrology illumination source 130 is a separate illumination source configured to generate a separate metrology illumination beam 132. The metrology illumination beam 132 may include one or more selected wavelengths of light including, but not limited to, ultraviolet (UV) radiation, visible radiation, or infrared (IR) radiation.

In another embodiment, the metrology illumination source 130 directs the metrology illumination beam 132 to a metrology sample 125 via an illumination pathway 134. As used throughout the present disclosure, the term "metrology sample" generally refers to an object to be inspected by the metrology sub-system 104. For example, the metrology sample 125 may include, but is not required to include, the lithography sample 124. In this regard, the metrology sub-system 104 may operate as a wafer inspection system. By way of another example, the metrology sample 125 may include a pattern mask (e.g. reticle). In this regard, the metrology sub-system 104 may operate as a reticle inspection system.

The illumination pathway 134 may include one or more lenses 136 or additional optical components 138 suitable for modifying and/or conditioning the metrology illumination beam 132. For example, the one or more optical components 138 may include, but are not limited to, one or more polarizers, one or more filters, one or more beam splitters, one or more diffusers, one or more homogenizers, one or more apodizers, or one or more beam shapers. In another embodiment, the metrology sub-system 104 includes an objective lens 140 to focus the metrology illumination beam 132 onto the metrology sample 125.

In another embodiment, the metrology sub-system 104 includes a detector 142 configured to capture radiation emanating from the metrology sample 125 through a collection pathway 144. For example, a detector 142 may receive an image of the lithography sample 124 provided by elements in the collection pathway 144 (e.g. the objective lens 140, lenses 146, or the like). By way of another example, a detector 142 may receive radiation reflected or scattered (e.g. via specular reflection, diffuse reflection, and the like) from the metrology sample 125. By way of another example, a detector 142 may receive radiation generated by the metrology sample 125 (e.g. luminescence associated with absorption of the metrology illumination beam 132, or the like). By way of another example, a detector 142 may receive one or more diffracted orders of radiation from the metrology sample 125 (e.g. 0-order diffraction, ±1 order diffraction, ±2 order diffraction, and the like).

The detector 142 may include any type of optical detector known in the art suitable for measuring illumination received from the metrology sample 125. For example, a detector 142 may include, but is not limited to, a CCD detector, a TDI detector, a photomultiplier tube (PMT), an avalanche photodiode (APD), or the like. In another embodiment, a detector 142 may include a spectroscopic detector suitable for identifying wavelengths of radiation emanating from the metrology sample 125. In another embodiment, the metrology sub-system 104 may include multiple detectors 142 (e.g. associated with multiple beam paths) generated by one or more beamsplitters to facilitate multiple metrology measurements (e.g. multiple metrology tools) by the metrology sub-system 104.

The collection pathway 144 may further include any number of optical elements to direct and/or modify illumination collected by the objective lens 140 including, but not limited to, one or more lenses 146, one or more filters, one or more polarizers, or one or more beam blocks.

In one embodiment, as illustrated in FIG. 1C, the metrology sub-system 104 may include a beamsplitter 148 oriented such that the objective lens 140 may simultaneously direct the metrology illumination beam 132 to the metrology sample 125 and collect radiation emanating from the metrology sample 125. In this regard, the metrology sub-system 104 may be configured in an epi-illumination mode. In another embodiment, the angle of incidence of the metrology illumination beam 132 on the metrology sample 125 is adjustable. For example, the path of the metrology illumination beam 132 through the beamsplitter 148 and the objective lens 140 may be adjusted to control the angle of incidence of the metrology illumination beam 132 on the metrology sample 125. In this regard, the metrology illumination beam 132 may have a nominal path through the beamsplitter 126 and the objective lens 140 such that the metrology illumination beam 132 has a normal incidence angle on the metrology sample 125. Further, the angle of incidence of the metrology illumination beam 132 on the metrology sample 125 may be controlled by modifying the position and/or angle of the metrology illumination beam 132 on the beamsplitter 148 (e.g. by rotatable mirrors, a spatial light modulator, a free-form illumination source, or the like). In another embodiment, the metrology illumination source 130 directs the one or more metrology illumination beams 132 to the metrology sample 125 at an angle (e.g. a glancing angle, a 45-degree angle, or the like).

In another embodiment, the metrology sub-system 104 is communicatively coupled to the controller 106 of system 100. In this regard, the controller 106 may be configured to receive data including, but not limited to, metrology data (e.g. metrology measurement results, images of the target, pupil images, and the like) or metrology metrics (e.g. precision, tool-induced shift, sensitivity, diffraction efficiency, through-focus slope, side wall angle, critical dimensions, and the like). In another embodiment, the controller 106 is communicatively coupled to the metrology illumination source 130 to direct the adjustment of the angle of incidence between the metrology illumination beam 132 and the metrology sample 125. In another embodiment, the controller 106 directs the metrology illumination source 130 to provide one or more selected wavelengths of illumination (e.g. in response to feedback).

In a general sense, the metrology sub-system 104 may include any type of metrology system known in the art such as, but not limited to, a spectroscopic ellipsometer with one or more angles of illumination, a spectroscopic ellipsometer for measuring Mueller matrix elements (e.g. using rotating compensators), a single-wavelength ellipsometer, an angle-resolved ellipsometer (e.g. a beam-profile ellipsometer), a spectroscopic reflectometer, a single-wavelength reflectometer, an angle-resolved reflectometer (e.g. a beam-profile reflectometer), an imaging system, a pupil imaging system, a spectral imaging system, or a scatterometer. Further, the metrology system may include a single metrology tool or multiple metrology tools. A metrology system incorporating multiple metrology tools is generally described in U.S. Pat. No. 7,478,019. Focused beam ellipsometry based on primarily reflective optics is generally described in U.S. Pat. No. 5,608,526, which is incorporated herein by reference in its entirety. The use of apodizers to mitigate the effects of optical diffraction causing the spread of the illumination spot beyond the size defined by geometric optics is generally described in U.S. Pat. No. 5,859,424, which is incorporated herein by reference in its entirety. The use of high-numerical-aperture tools with simultaneous multiple angle-of-incidence illumination is generally described by U.S. Pat. No. 6,429,943, which is incorporated herein by reference in its entirety. Quantifying imaging performance in high NA optical lithography is generally described in Lee, et al., "Quantifying imaging performance bounds of extreme dipole illumination in high NA optical lithography", Proc. of SPIE Vol. 9985 99850X-1 (2016), which is incorporated herein by reference in its entirety.

Figure 2:
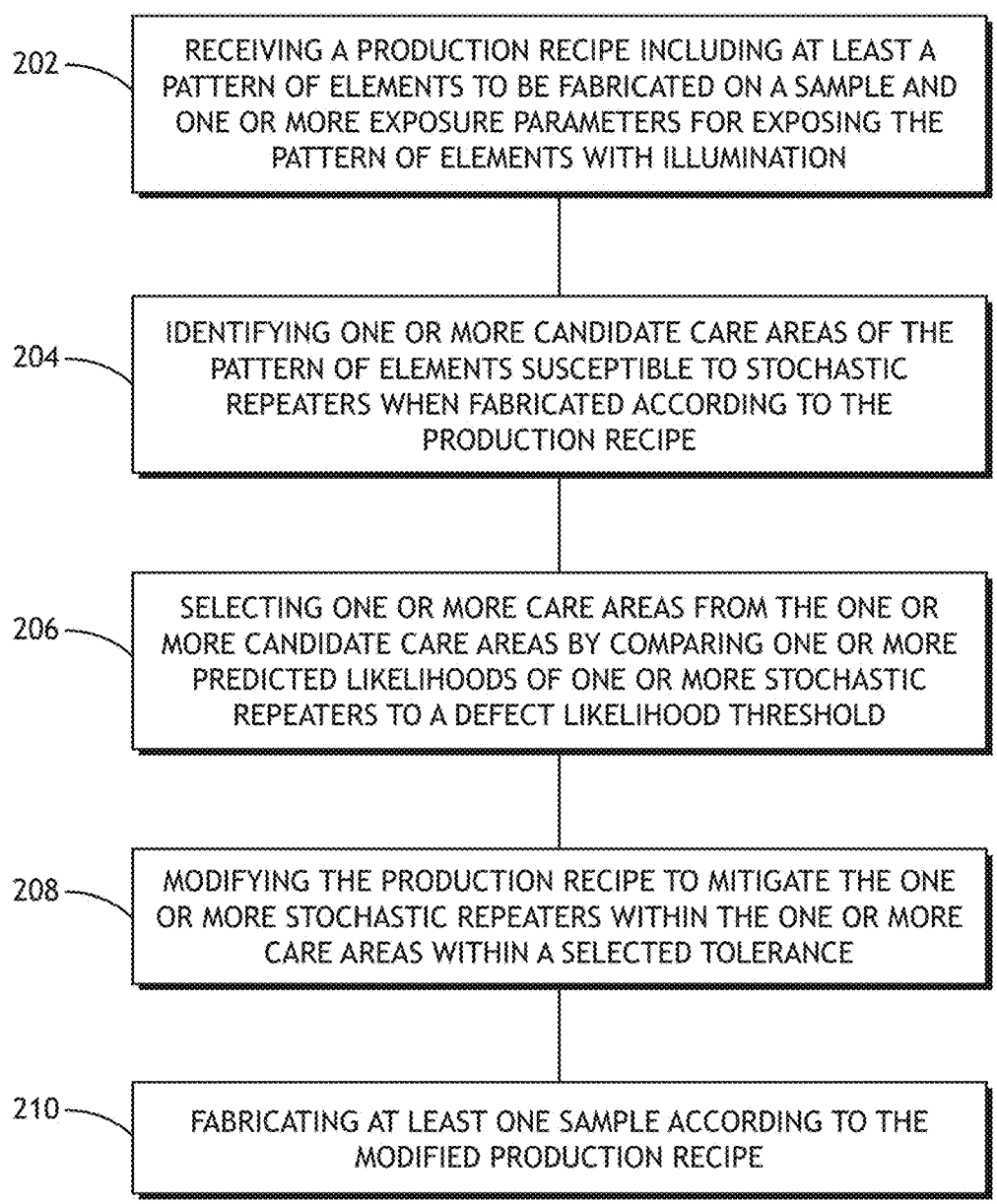
FIG. 2 is a flow diagram illustrating steps performed in a method for stochastically-aware metrology, in accordance with one or more embodiments of the present disclosure.

FIG. 2 is a flow diagram illustrating steps performed in a method 200 for stochastically-aware metrology, in accordance with one or more embodiments of the present disclosure. Applicant notes that the embodiments and enabling technologies described previously herein in the context of system 100 should be interpreted to extend to method 200. It is further noted, however, that the method 200 is not limited to the architecture of system 100.

In one embodiment, method 200 includes a step 202 of receiving a production recipe including at least a pattern of elements to be fabricated on a sample and one or more exposure parameters for exposing the pattern of elements with illumination.

The pattern of elements to be fabricated on the sample (e.g. lithography sample 124 of system 100) may include any type of features. For example, the pattern of elements may include one or more device elements corresponding to features to be fabricated as part of an operational semiconductor device or one or more metrology targets (e.g. one or more overlay targets, one or more exposure-sensitive targets, one or more targets sensitive to the focal position of the sample, or the like). In this regard, the susceptibility of any portion of the pattern of elements to stochastic repeaters may be characterized.

Further, the exposure parameters may include, but are not limited to, the wavelength of the illumination source, the illumination dose (e.g. energy per area incident on the sample), the focal position of the sample (e.g. within the lithography sub-system 102, or the like), the exposure time, the spatial profile of the illumination source, or the spatial distribution of illumination on the sample.

In a general sense, the production recipe may be received from a single location or multiple locations. For example, the production recipe may be received from a memory device (e.g. a file stored on a memory device). Taking system 100 as an example, the production recipe may be received by the controller 106 from memory device 110. Further, the production recipe may be received from a local memory device (e.g. located in a common housing with the controller 106) or from a remote memory device (e.g. a recipe management system connected to the controller via a network, or the like). Additionally, portions of the production recipe may be received from different locations. For example, the pattern of elements to be fabricated on the sample may be associated with a device design file stored on a memory device including, but not limited to, a geometric layout of features on one or more layers, material properties associated with one or more layers, or electrical connections between features on one or more layers.

In another embodiment, method 200 includes a step 204 of identifying one or more candidate care areas of the pattern of elements susceptible to stochastic variations (e.g. stochastic repeaters) when fabricated according to the production recipe. In this regard, candidate care areas may include fabrication defects predicted to occur stochastically when fabricated according to the production recipe as described previously herein. Accordingly, candidate care areas may correspond to locations at which one or more defects may occur stochastically. For example, candidate care areas may include both failure points associated with deterministic repeaters (e.g. defects predicted to occur for each fabrication run in the same location) as well as identified weak points that may be susceptible to stochastic repeaters. Identified weak points may include features within the pattern of elements (e.g. particular sizes or shapes of elements, distances between particular elements, or the like) that may be within specification, but are far from nominal values.

Candidate care areas susceptible to stochastic repeaters may be associated with either a pattern mask (e.g. a reticle) including the pattern of elements to be exposed on a wafer or a wafer after any production step (e.g. ADI or AEI of any layer). For example, the identification of candidate care areas on a reticle susceptible to stochastic repeaters may be utilized in a print check process to enable corrective actions (e.g. modification of the production recipe to mitigate the fabrication of stochastic defects or the generation of metrology recipes to monitor stochastic defects) prior to wafer fabrication. By way of another example, the identification of candidate care areas on a wafer susceptible to stochastic repeaters may be utilized in any process-monitoring application including, but not limited to, hot spot identification, a PWG analysis, or a WET analysis.

Figure 3:
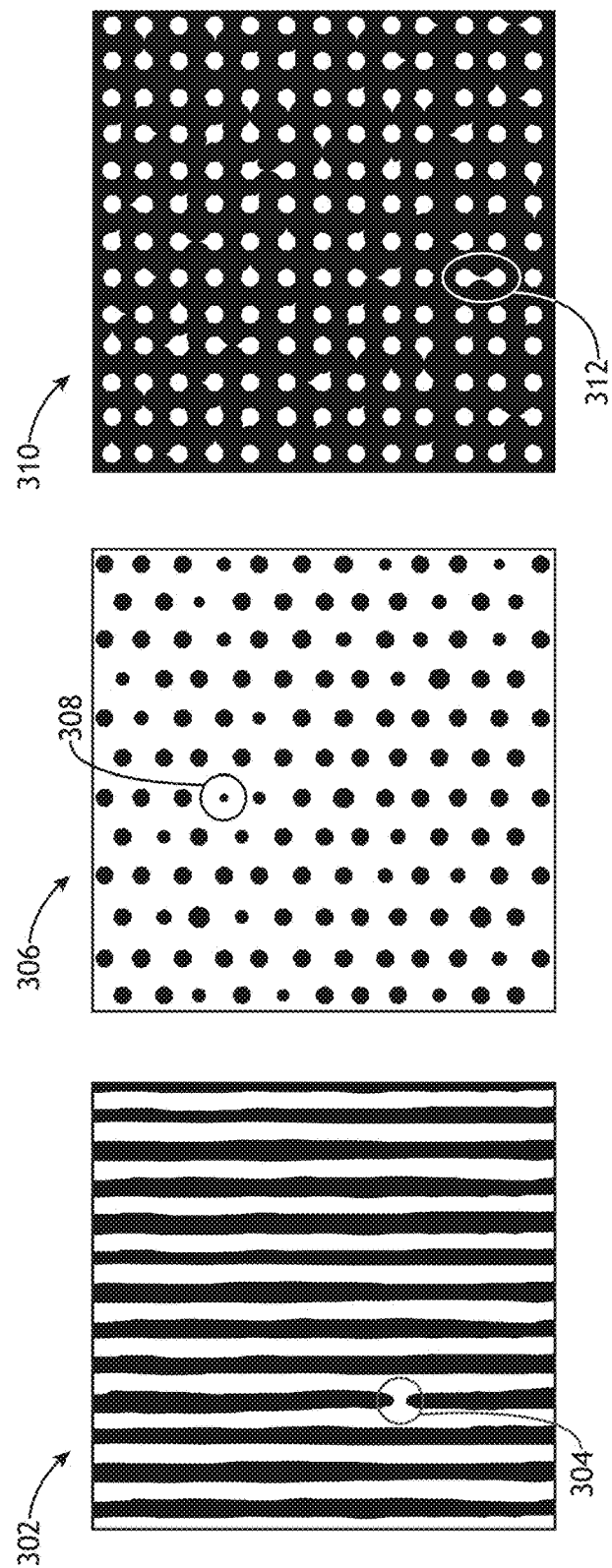
FIG. 3 includes example images of stochastic repeaters on fabricated samples, in accordance with one or more embodiments of the present disclosure.

Candidate care areas identified in step 204 may include any type of predicted stochastic repeater known in the art. FIG. 3 includes conceptual illustrations of stochastic repeaters on fabricated samples, in accordance with one or more embodiments of the present disclosure. For example, illustration 302 includes a line-space pattern and stochastic variations of the fabrication process may lead to random undesired connections (e.g. electrical shorts, or the like) between elements of the line-space pattern such as stochastic repeater 304. By way of another example, illustration 306 includes a periodic distribution of holes. In this example, each hole in illustration 306 is designed to be a circular hole with a common radius, but stochastic variations in the fabrication process may result in variations of the size or shape of the fabricated holes. Stochastic repeater 308 includes a partially-filled hole. By way of another example, illustration 310 includes a periodic distribution of columns intended to have a circular profile and a common radius. In this example, stochastic variations in the fabrication process may result in variations of the size or shape of fabricated columns or undesired connections between adjacent columns indicated by stochastic repeater 312. It is to be understood that the examples provided in FIG. 3 and the accompanying description are provided solely for illustrative purposes and should not be interpreted as limiting the present disclosure in any way. For example, stochastic repeaters may include variations of the placement and/or the roughness of feature edges associated with uncertainty in energy absorbed about the edge as well as a sensitivity of edge position to absorbed energy. By way of another example, stochastic repeaters may include bridging defects (e.g. nano-bridging, micro-bridging, or the like) in line/space or tip-to-tip structures. In a general sense, a stochastic repeater may include any type of fabrication defect that manifests stochastically during fabrication.

A stochastic repeater may have any number of root causes associated with a fabrication process. For example, an uncertainty associated with the absorption of photons in a given volume of the sample (e.g. a resist layer) may be characterized by the photon shot noise (PSN):

$$PSN = \frac{1}{\sqrt{\langle n \rangle_{abs}}} = \frac{1}{\sqrt{\alpha \cdot D \cdot V \cdot \lambda / hc}} \quad (1)$$

where $\langle n \rangle_{abs}$ is the average number of absorbed photons absorbed in a volume V, $\alpha$ is the absorbance of the sample, D is the dose (e.g. energy incident on the sample per incident area), $\lambda$ is the wavelength of illumination (e.g. from the lithography illumination source 112, or the like), h is Planck's constant, and c is the speed of light. As equation 1 indicates, decreasing the illumination wavelength ($\lambda$) to decrease the size of printed features (e.g. decreased V) results in an increase of the PSN. Accordingly, the likelihood of stochastic repeaters associated with the uncertainty of photon absorption may increase with decreased illumination wavelength.

Equation 1 further indicates that decreasing the dose of energy on the sample (e.g. associated with the intensity and/or power of the illumination source) may further increase the PSN and thus increase the likelihood of stochastic repeaters. It is typically desirable, particularly in high-volume manufacturing environments, to decrease the illumination dose on the sample to the extent possible while maintaining sufficient dose to fabricate desired structures according to specified tolerances (e.g. tolerances on the dimensions and spacing of fabricated structures, tolerances on the allowable number of defects, and the like). Minimizing the illumination dose in this way may provide multiple benefits for high volume manufacturing such as, but not limited to, increased throughput by reducing the required exposure time per sample and decreased cost. It is recognized herein that illumination sources, and particularly EUV illumination sources, may have high operational costs associated with energy demands and maintenance costs. In this regard, it is typically desirable to select an illumination dose providing a balance between the benefits of decreased illumination dose and negative impacts of the decreased illumination dose such as increased stochastic repeaters. It is further recognized herein that the focal position of the sample during an exposure step (e.g. in the lithography sub-system 102, or the like) may influence the PSN. For example, variations in the focal position of the sample from a nominal focal position may result in increased blur associated with imaging pattern elements from a pattern mask to the sample (e.g. a modification of the size and/or shape of the point spread function of the lithography sub-system 102). Accordingly, variations in the focal position of the sample may modify the photon density on the sample and impact the PSN.

Figure 4:
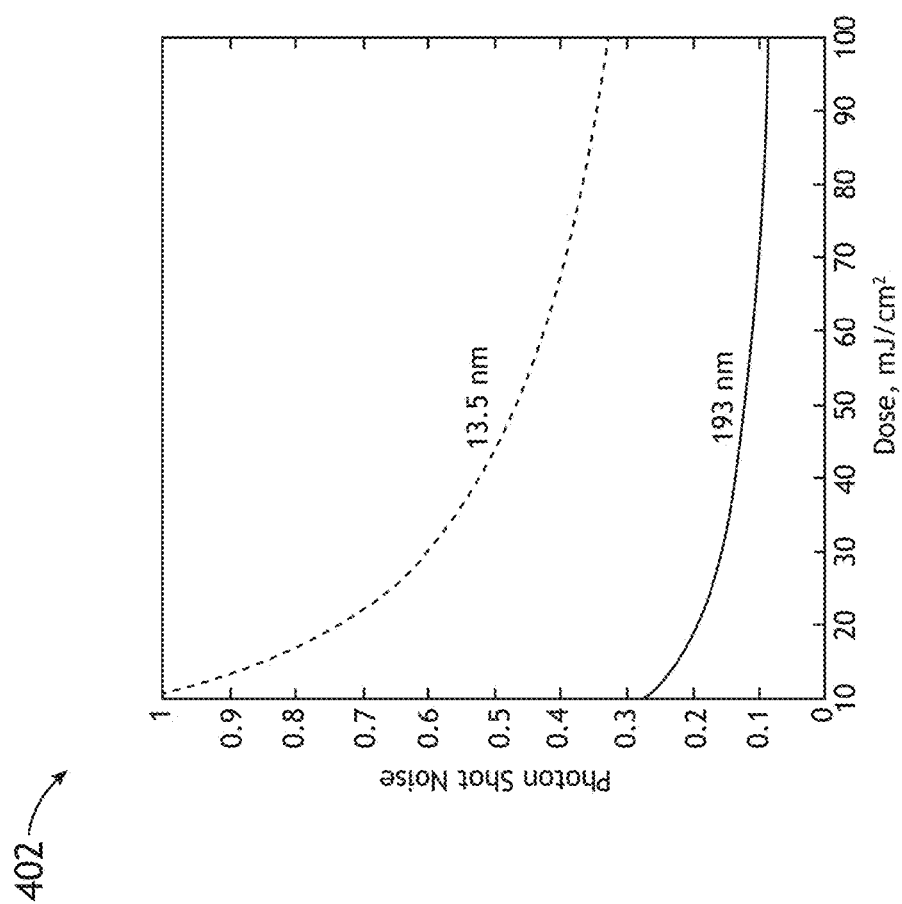
FIG. 4 is a plot illustrating calculated PSN associated with absorption of irradiation into a 3 nm cube of photoresist as a function of dose for wavelengths of 193 nm and 13.5 nm, in accordance with one or more embodiments of the present disclosure.

FIG. 4 is a plot 402 illustrating calculated PSN associated with absorption of illumination into a 3 nm cube of photoresist as a function of dose for wavelengths of 193 nm (e.g. generated by an ArF illumination source) and 13.5 nm (e.g. generated using an EUV illumination source), in accordance with one or more embodiments of the present disclosure. For both illumination wavelengths illustrated in FIG. 4, decreasing the dose on the sample leads to an increase in the PSN. However, this trend is more pronounced for smaller illumination wavelengths as indicated by a more substantial increase in PSN with decreasing dose for 13.5 nm illumination compared to 193 nm illumination. Accordingly, decreasing the illumination wavelength to enable the fabrication of smaller features may require increased consideration of stochastic repeaters when determining illumination dose.

An additional root cause of stochastic repeaters may be associated with stochastic variations within the photoresist (e.g. resist layer 128, or the like). For example, a photoresist may include photoacid generators (PAGs) that absorb incident illumination and provides a change in solubility of exposed regions corresponding to the amount of absorbed energy. In this regard, the solubility of exposed and unexposed regions of the photoresist may differ and a subsequent etch step may selectively remove either the exposed or unexposed regions to develop features on the sample. Typically, PAGs are not continuous throughout the photoresist, but rather consist of molecules distributed throughout the photoresist. Accordingly, as the size of fabricated features decreases, the impact of variations in the actual positions of PAG molecules may increase and stochastic repeaters associated with the PAG molecules may correspondingly increase.

Further, the final distribution of acid in response to an incident photon (e.g. a distribution of modified solubility) may exhibit stochastic variations due to electron ionization within the sample. In particular, a photon having photon energy exceeding the ionization threshold of a photoresist may induce a cascade of electrons of varying energies based on the photoelectric effect. This cascade of electrons may then interact with the PAG in different ways depending on the energy to further impact solubility. Accordingly, more than one acid molecule may be generated by PAGs in response to a single photon (e.g. the acid yield may be greater than 1). Typically, photoresist materials have an ionization threshold in the UV or EUV range such that the impact of electron ionization may become significant for illumination wavelengths in this UV or EUV range, which may produce spatial blurring of the absorbed energy.

Figures 5A, 5B:
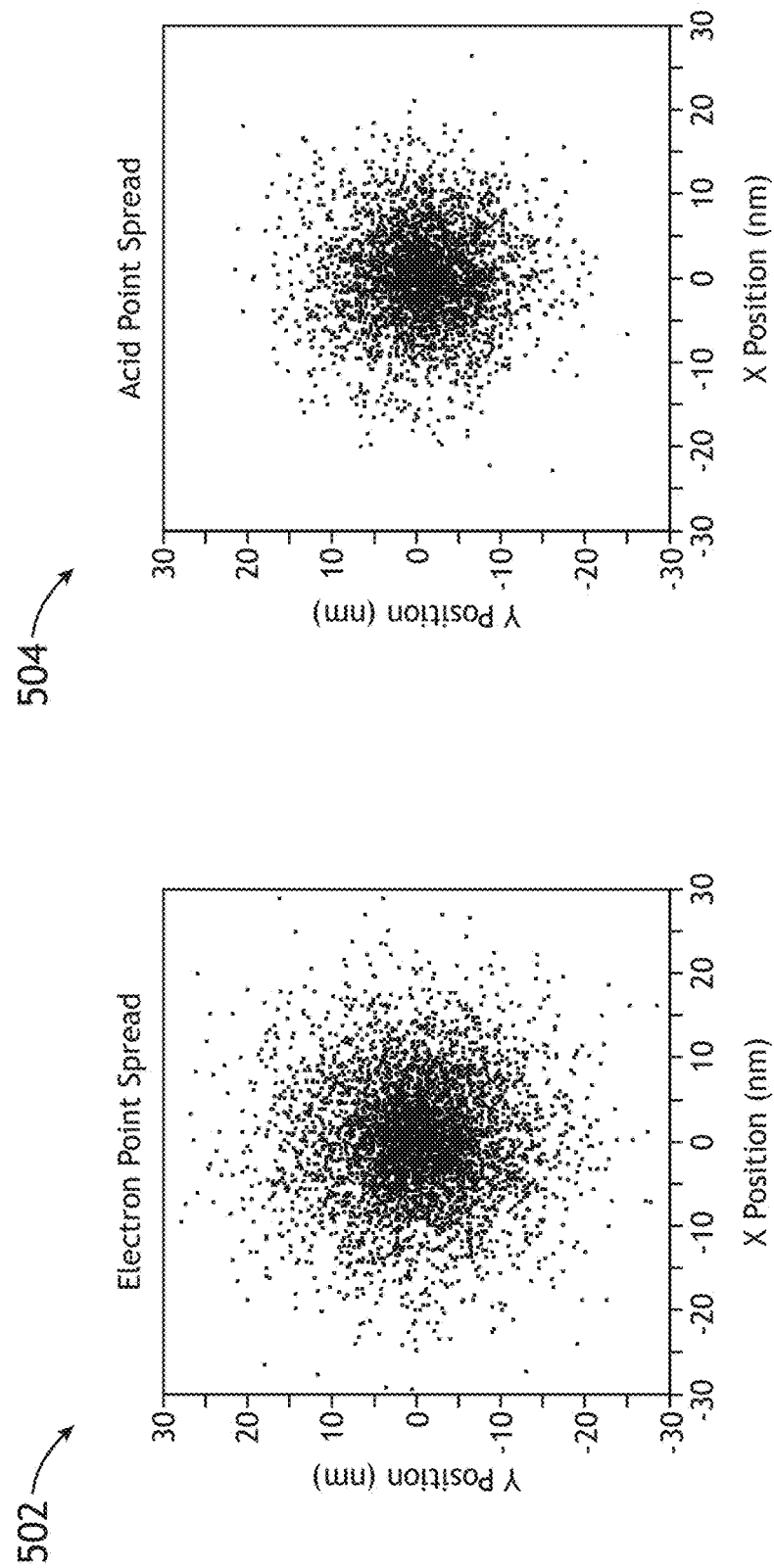
FIG. 5A is a plot of electron point spread in a photoresist in response to illumination with a wavelength of 124 nm based on physical simulations of multiple controlled discrete photon absorption events, in accordance with one or more embodiments of the present disclosure.
FIG. 5B is a plot of the acid point spread in a photoresist in response to illumination with a wavelength of 124 nm including the impact of electron scattering illustrated in FIG. 5A, in accordance with one or more embodiments of the present disclosure.

FIG. 5A is a plot 502 of simulated electron point spread in a photoresist in response to illumination with a wavelength of 124 nm (10 eV) based on physical simulations of multiple controlled discrete photon absorption events, in accordance with one or more embodiments of the present disclosure. FIG. 5A clearly demonstrates that electron scattering associated with the ionization of electrons within the photoresist may lead to a redistribution, or blurring, of absorbed energy within the material. Here, energy is highly concentrated in a 10-20 nm region, though energy is distributed throughout at least a 60 nm region. FIG. 5B is a plot 504 of the acid point spread in a photoresist in response to illumination with a wavelength of 124 nm (10 eV) including the impact of electron scattering illustrated in FIG. 5A, in accordance with one or more embodiments of the present disclosure. The concentration of acids generated by PAG molecules through absorption of either photons or electrons exhibits a similar distribution to the electron point spread in FIG. 5A, though the dimensions of the acid spread may be slightly smaller because not every single ionized electron may give rise to an acid molecule (e.g. some electrons may be thermally absorbed, or the like). As described previously herein, the point spread of acid molecules may increase stochastic variations within the photoresist and may lead to increased stochastic repeaters. Additionally, further decreasing the illumination wavelength may lead to further stochastic variations.

Figure 6B:
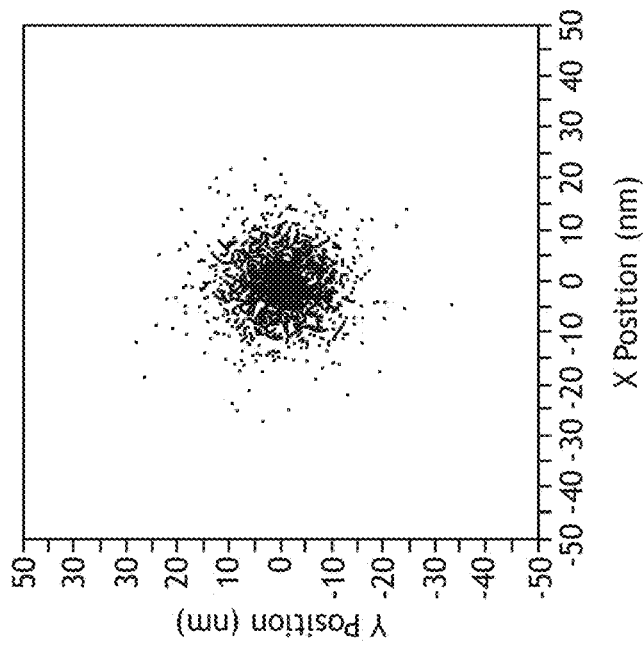
FIG. 6B is a plot of the electron point spread within a photoresist in response to a single simulation of the absorption of 1000 photons, in accordance with one or more embodiments of the present disclosure.
Figure 6A:
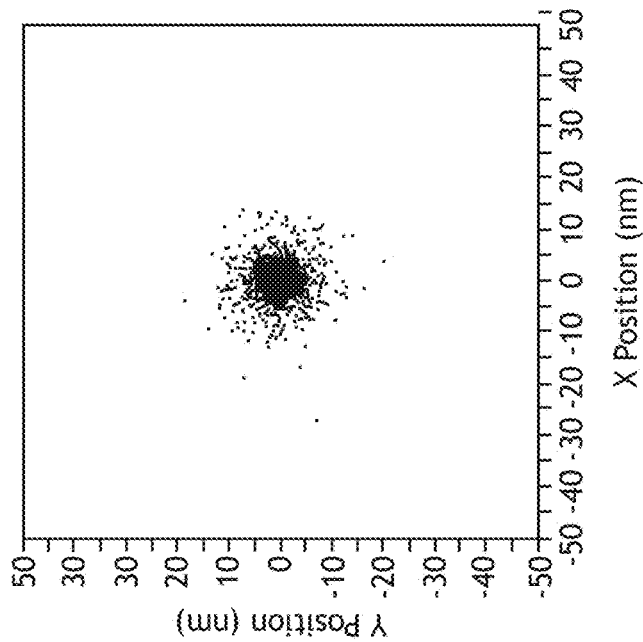
FIG. 6A is a plot of the electron point spread within a photoresist in response to 1000 simulations of single photon absorption, in accordance with one or more embodiments of the present disclosure.

Further, both the concentration of PAG molecules in a photoresist (e.g. PAG loading) as well as the exposure conditions of the production recipe (e.g. illumination dose and exposure time) may additionally impact the production of stochastic repeaters. FIG. 6A is a plot 602 of the simulated electron point spread within a photoresist in response to 1000 simulations of single photon absorption, in accordance with one or more embodiments of the present disclosure. FIG. 6B is a plot 604 of the electron point spread within a photoresist in response to a single simulation of the absorption of 1000 photons, in accordance with one or more embodiments of the present disclosure. Table 1 includes electron scattering data for both simulations.

|  | 1000 Simulations of 1 absorbed photon (Plot 602) | 1 Simulation of 1000 absorbed photons (Plot 604) |
|---|---|---|
| Electrons Generated | 3277 | 3734 |
| Electron Quantum Yield | 3.28 | 3.73 |
| Electron Distance - Mean (nm) | 3.26 | 5.98 |
| Electron Distance - Max (nm) | 28.51 | 43.94 |

The total amount of absorbed energy is the same for both simulations; however, the simulation of plot 602 may represent a low-power, long-exposure production recipe, whereas the simulation of plot 604 may represent a high-power, short-exposure production recipe. Further, the electron scattering characteristics (e.g. the distances electrons travel from the absorption site and thus the spatial extent of the energy redistribution) may differ for low-power and the high-power exposures. In particular, high-power exposure may generate a larger number of ionized electrons than low-dose exposure. Further, the spatial extent of the energy redistribution may be significantly larger for high-power illumination, particularly the maximum electron distance. In this regard, high-power illumination may be more susceptible to stochastic variations during fabrication, and thus stochastic repeaters, compared to low-power illumination due to the larger redistribution or blur-length of absorbed energy. Excessive blurring of the absorbed energy may represent a loss in the contrast or degradation of the projected optical image.

In another embodiment, step 204 includes identifying candidate care areas by simulating the fabrication of the pattern elements on a sample. The step 204 may include identifying candidate care areas using stochastic computational lithography with a variety of algorithms. For example, optical interaction of incident illumination (e.g. illumination beams 114, or the like) with a sample (e.g. lithography sample 124), or the like) may be modeled using an electromagnetic (EM) solver. Further, the EM solver may utilize any method known in the art including, but not limited to, rigorous coupled-wave analysis (RCWA), finite element method analysis, method of moments analysis, a surface integral technique, a volume integral technique, or a finite-difference time-domain analysis. By way of another example, optical interaction of incident illumination with a sample may be modeled using Monte Carlo techniques. The stochastic simulation may characterize impacts of stochastic processes such as, but not limited to, uncertainties associated with the absorption of photons by the sample, the distribution of PAGs in the sample, or energy redistribution due to ionization in the sample as described previously herein. For example, computational lithography simulations may be, but are not required to be, performed by the PROLITH software product provided by KLA-TENCOR.

In another embodiment, the step 204 includes identifying candidate care areas by analyzing the design of the pattern of elements in the production recipe to determine areas susceptible to stochastic repeaters. For example, step 204 may include a simulation of the placement of edges in the pattern of elements (e.g. edge roughness) based on characterizing the uncertainty of energy absorption about an edge and a sensitivity of edge placement to absorbed energy. In this regard, a simulation of edge roughness may provide insight into the susceptibility of a wide range of features to stochastic defects (e.g. line-space features, holes, or columns). A calculation of an uncertainty of energy absorption about an edge may be based on any number of factors such as, but not limited to, PSN. Further, a calculation of the sensitivity of edge placement to energy absorption may be based on any number of factors such as, but not limited to, the geometry of pattern elements (e.g. degree of curvature, sharp edges, or the like), PAG loading, or electron ionization. It is recognized herein that this analysis of the design of the pattern of elements may be, but is not required to be, a faster simulation that is less computationally intensive than a more rigorous computational lithography analysis. Thus, step 204 may include such fast simulation algorithms, more rigorous simulation algorithms, or a combination of algorithms depending on a desired balance of precision and computational requirements.

The step 204 may include any number of inputs for identifying candidate care areas using stochastic simulations and/or analysis of the design of the pattern of elements. For example, the design of the pattern of elements may be, but is not required to be, included within a design file received in step 202.

Additionally, inputs of step 204 may include a representation of the irradiance distribution in the photoresist in two or three dimensions. This irradiance distribution may be obtained through simulations and/or through measurements. For example, inputs may include, but are not limited to, material parameters of sample layers such as film thickness and real/imaginary parts of the refractive indices of sample layers. By way of another example, inputs may include a representation of the illumination profile (e.g. the source shape, numerical aperture, flare, and the like). By way of another example, inputs may include pattern mask layouts (e.g. including optical proximity correction structures, sub-resolution assist features, or the like) and a 3D mask stack.

Further, inputs of step 204 may include an approximation of process blur associated with a fabrication system to be applied to the irradiance distribution in the photoresist. For example, the process blur may take the form of a constant Gaussian convolution kernel or dose-dependent blur.

In another embodiment, step 204 includes identifying candidate care areas by inspecting one or more samples (e.g. using metrology sub-system 104, or the like) to determine areas susceptible to stochastic repeaters. For example, step 204 may include inspecting a pattern mask (e.g. a reticle) to identify portions of the pattern of elements on the pattern mask that may lead to stochastic defects when printed on a wafer. In this regard, the candidate care areas may include portions of the pattern mask that may not be expected to produce a deterministic defect, but may deviate from the nominal design and may thus be susceptible to stochastic defects when printed with selected exposure conditions. By way of another example, step 204 may include inspecting one or more printed wafers to identify areas that may print within a selected specification (e.g. a critical dimension, a side-wall angle, or the like), but deviate from nominal design values such that the areas may be susceptible to stochastic variations across multiple printing steps.

In another embodiment, method 200 includes a step 206 of selecting one or more care areas from the one or more candidate care areas by comparing one or more predicted likelihoods of one or more stochastic repeaters to a defect likelihood threshold. As described previously herein, the candidate care areas identified in step 204 and thus the care areas selected in step 206 may be associated with the pattern mask and/or a wafer at any point in the fabrication process (e.g. ADI, AEI, or the like). Stochastic repeaters associated with a particular pattern element may occur with any probability distribution as a function of location on a sample or as a function of the number of fabrication runs (e.g. a Poisson distribution, a Gaussian distribution, or the like). The step 206 may thus include analyzing each of the candidate care areas identified in step 204 to predict a probability of stochastic repeaters in the candidate care areas. Further, step 206 may include selecting care areas based on a defect likelihood threshold. The defect likelihood threshold may include a threshold probability of stochastic repeaters based on any metric. For example, step 206 may include selecting care areas including defects predicted to print in a selected percentage of production runs (e.g. 50%, 10%, 1%, 0.1%, 0.001%, or the like) when fabricated according to a selected production recipe (e.g. fabricated with selected exposure conditions including dose, illumination profile, focal position within a lithography sub-system 102, or the like).

As an illustrative example, it may be the case that the probability that a particular pattern element is fabricated with a defect may have a Poisson distribution as a function of dose. Accordingly, the pattern element may nearly always print with a defect (e.g. a deterministic repeater) for sufficiently low dose values due to insufficient exposure. Similarly, the pattern element may nearly never print with a defect for sufficiently high dose values due to adequate exposure. However, it may be the case that the defect may print stochastically over a certain range of dose values between these extreme cases and thus be a stochastic repeater. The step 206 may thus include selecting one or more care areas from the candidate care areas identified in step 204 based on a defect likelihood threshold probability of stochastic repeaters when fabricated with a selected dose.

It is to be understood that the above example of a dose-dependent stochastic repeater is provided solely for illustrative purposes and should not be interpreted as limiting. In a general sense, a probability that a defect may print may be influenced by a wide range of exposure conditions (e.g. dose, illumination profile, focal position within a lithography sub-system 102, or the like). Accordingly, step 206 may thus include selecting one or more care areas based on a defect likelihood threshold probability of stochastic repeaters when fabricated with a selected set of exposure conditions.

The probability that a candidate care area prints with one or more defects (e.g. a likelihood of a stochastic repeater) may be predicted in step 206 using any technique known in the art. In one embodiment, the likelihood of a stochastic repeater in a candidate care area is determined by simulating the fabrication of the candidate care area according to the production recipe using a stochastic simulation (e.g. stochastic computational lithography incorporating EM solvers, Monte Carlo techniques, analysis of the design of pattern elements, or the like).

For example, step 204 may include identifying candidate care areas by a relatively fast simulation technique (e.g. analyzing the design of the pattern of elements as described previously herein, or the like), and step 206 may include selecting care areas from the candidate care areas based on a more rigorous simulation technique (e.g. a computational lithography simulation, or the like). In this regard, the relatively fast simulation technique in step 204 may reduce the computational burden and thus the throughput of a more rigorous simulation in step 206. By way of another example, step 204 may include identifying candidate care areas by inspecting one or more fabricated samples (e.g. a pattern mask containing the pattern of elements to be printed on a wafer, a printed wafer, or the like), and step 206 may include selecting care areas from the candidate care areas based on a stochastic simulation of the candidate care areas identified based on metrology. In this regard, simulations may provide insight into the likelihood of stochastic repeaters identified as weak points (e.g. patterns that may print within specification, but may be far from nominal values) based on actual fabrication processes.

In another embodiment, the fabrication probability of a stochastic repeater in a candidate care area is determined by inspecting the candidate care areas identified in step 204 on one or more printed wafers to determine a predicted likelihood of stochastic repeaters. For example, step 204 may include identifying candidate care areas based on stochastic simulations (e.g. relatively fast simulations and/or relatively rigorous simulations as described previously herein), and step 206 may include selecting care areas based on inspecting the identified candidate care areas on one or more wafers fabricated according to the production recipe. In this regard, step 204 may include simulations to guide the physical inspection (e.g. with lithography sub-system 102, or the like) of wafers in step 206. Further, step 206 may include fabricating a series of wafers with a range of exposure conditions (e.g. dose, focal position, illumination profile, or the like) or a range of pattern element modifications (e.g. varying optical parameter correction (OPC), sub-resolution assist features (SRAFs), or the like) designed to minimize the likelihood of stochastic repeaters, or the like). Thus, step 206 may include the inspection of the candidate care area fabricated according to multiple production recipes to predict the likelihood of stochastic repeaters.

In another embodiment, the probability of a stochastic repeater in a candidate care area is determined by comparing the layout of elements in the candidate care area to a library of pattern layouts having predicted likelihoods for stochastic repeaters. Accordingly, a probability of stochastic repeaters in a candidate care area may be analyzed based on a comparison to training data that may be, but is not required to be, generated by simulations and/or measurements of fabricated samples. For example, the candidate care areas may be analyzed using data fitting and optimization techniques including, but not limited to libraries, fast-reduced-order models, regression, machine-learning algorithms such as deep learning techniques, neural networks, support-vector machines (SVM), dimensionality-reduction algorithms (e.g. principal component analysis (PCA), independent component analysis (ICA), local-linear embedding (LLE), and the like), sparse representation of data (e.g. Fourier or wavelet transforms, Kalman filters, algorithms to promote matching from same or different tool types, and the like). The candidate care area analysis may be, but is not required to be, performed by the Signal Response Metrology (SRM) software product provided by KLA-TENCOR. Additionally, candidate care area data may be provided by any source such as, but not limited to, the design of pattern elements from a design file, simulations, or physical inspections of fabricated samples (e.g. pattern masks or wafers).

In another embodiment, the candidate care areas identified in step 204 and/or the care areas selected in step 206 may be inserted into the library of pattern layouts having predicted likelihoods of stochastic repeaters. In this regard, the library may be updated and/or trained with stochastic simulations, metrology results, and/or metrology-verified simulations.

In another embodiment, step 206 includes ranking stochastic repeaters found in one or more candidate care areas based on the predicted defect likelihoods as a function of location on a sample. It is recognized herein that the likelihood that a particular pattern will fabricate with a defect (e.g. as stochastic repeater) may vary based on the location on a sample. Certain patterns may print poorly (with a higher probability of a defect) only in certain locations on a sample, whereas other patterns may print poorly at nearly all locations on a sample. Thus, data associated with a ranking of stochastic repeaters as a function of sample location may be provided (e.g. in as feed-forward data) to generate sampling plans for a metrology system to sensitively monitor the stochastic repeaters.

In another embodiment, the care areas selected in step 206 may be fed back to improve and/or train a stochastic simulation model (e.g. a stochastic simulation model used in step 204 and/or step 206) to improve predictive accuracy and/or efficiency. Accordingly, selecting care areas based on a combination of simulation of the fabrication of the pattern of elements and inspection of pattern elements fabricated under the same conditions may provide iterative feedback to continually improve stochastic simulation models.

In another embodiment, the care areas selected in step 206 may be used to generate metrology recipes (e.g. to be used by metrology sub-system 104, or the like). It is recognized herein that metrology recipes may include sampling plans developed to characterize one or more aspects of samples during fabrication (e.g. to monitor defects, to monitor overlay between layers, or the like) at a selected number of representative locations on a sample. The number and specific locations of the sampling plan may typically be based on a balance of accuracy with throughput. However, it is further recognized herein that sampling plans developed to characterize deterministic repeaters (e.g. defects occurring consistently at a given location for nearly all production runs) may be ill-suited to characterize stochastic repeaters that may fabricate with different probabilities at different locations of a sample. In one embodiment, the care areas selected in step 206 are used to generate sampling plans including locations to be inspected on a wafer suitable for monitoring stochastic repeaters at any stage of a production process. For example, sampling plans developed in accordance with inventive concepts provided herein may incorporate the probabilities of various stochastic repeaters as a function of location to provide sensitive and efficient monitoring of stochastic repeaters during fabrication.

Further, data associated with the care areas including stochastic repeaters (e.g. locations of care areas, probabilities of stochastic repeaters within the care areas, or the like) may be provided to additional tools in the production line (e.g. as feed-forward data). For example, the care areas may be provided to metrology tools for measuring one or more samples (e.g. reticles and/or wafers) according to a sampling plan. By way of an additional example, data associated with the care areas including stochastic repeaters may be provided to hot spot verification tools to identify portions of a wafer susceptible to defects (e.g. deterministic and/or stochastic defects) due to process errors, wafer contamination, or the like.

In another embodiment, method 200 includes a step 208 of modifying the production recipe to mitigate predicted occurrences of the one or more stochastic repeaters within the one or more care areas within a selected tolerance. It may be the case that a particular device be fabricated within a selected tolerance defining an acceptable number of defects (stochastic repeaters and/or deterministic repeaters). Accordingly, step 208 may include modifying at least one aspect of the production recipe such that the device may be fabricated according to the selected tolerance when taking into account stochastic repeaters.

In one embodiment, modifying the production recipe includes modifying one or more exposure conditions (e.g. dose, focal position in the lithography sub-system 102, illumination conditions, or the like) to mitigate stochastic repeaters. For example, step 208 may include increasing the illumination dose for one or more portions of the sample (e.g. associated with care areas selected in step 206) to reduce the likelihood of stochastic repeaters within the selected tolerance.

In another embodiment, modifying the production recipe includes modifying the pattern of elements to be fabricated to mitigate stochastic repeaters. For example, one or more features within the pattern of elements may be modified and/or replaced with alternative pattern layouts less susceptible to stochastic repeaters. Alternative pattern layouts may be selected using any technique known in the art. For example, alternative pattern layouts may be selected based on a library of pattern layouts with known susceptibilities to stochastic repeaters. By way of another example, the pattern mask may be modified to include sub-resolution features (OPC features, SRAFs, or the like) suitable for increasing printability of the pattern of elements on the lithography sample 124. In this regard, pattern mask elements with dimensions (e.g. actual dimensions, separations between pattern mask elements, or the like) smaller than a resolution of the lithography sub-system 102 may influence a pattern printed on a resist layer of a sample based on optical effects such as scattering or diffraction. For example, sub-resolution features may influence one or more characteristics of printed elements (e.g. PPE, sidewall angle, critical dimension, or the like) without being resolvably imaged onto the lithography sample 124. Further, sub-resolution features may influence the range of exposure conditions over which the pattern of elements may be fabricated within selected tolerances (e.g. the process window). In this regard, sub-resolution features may facilitate the robust fabrication of the designed pattern of elements on the lithography sample 124 without the sub-resolution elements themselves being resolvably printed.

In another embodiment, method 200 includes a step 210 of fabricating at least one sample according to the modified production recipe. Accordingly, any stochastic repeaters may be characterized and modified samples may be fabricated within selected tolerances, even when considering stochastic repeaters.

The herein described subject matter sometimes illustrates different components contained within, or connected with, other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "connected", or "coupled", to each other to achieve the desired functionality, and any two components capable of being so associated can also be viewed as being "couplable", to each other to achieve the desired functionality. Specific examples of couplable include but are not limited to physically interactable and/or physically interacting components and/or wirelessly interactable and/or wirelessly interacting components and/or logically interactable and/or logically interacting components.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes. Furthermore, it is to be understood that the invention is defined by the appended claims.

What is claimed:

1. A system comprising:
a controller configured to communicatively couple to a fabrication tool, the controller including one or more processors configured to execute program instructions causing the one or more processors to:
receive a production recipe including at least a pattern of elements to be fabricated on a sample using a selected lithography tool and one or more exposure parameters for exposing the pattern of elements during fabrication;
identify one or more candidate care areas including portions of the pattern of elements susceptible to stochastic repeaters by analyzing uncertainty of energy absorption in the sample and sensitivity of the pattern of elements to variations in absorbed energy, the stochastic repeaters including one or more portions of the pattern of elements predicted to exhibit stochastic fabrication errors;
select one or more care areas from the one or more candidate care areas for mitigation based on predicted likelihoods of the stochastic repeaters in the one or more care areas when fabricated according to the production recipe using the selected lithography tool;
modify the production recipe to mitigate the stochastic repeaters within the one or more care areas; and
direct the fabrication tool to fabricate at least one sample according to the modified production recipe.

2. The system of claim 1, wherein selecting one or more care areas from the one or more candidate care areas for mitigation comprises:
simulating fabrication of the one or more candidate care areas on one or more simulated samples according to the production recipe to determine one or more simulated stochastic repeaters; and
selecting the one or more care areas from the one or more candidate care areas based on predicted likelihoods of the one or more simulated stochastic repeaters.

3. The system of claim 2, wherein selecting one or more care areas from the one or more candidate care areas for mitigation further comprises:
simulating fabrication of the one or more candidate care areas with variations of the one or more exposure parameters from the production recipe to determine boundary exposure parameters for the simulated stochastic repeaters; and
selecting the one or more care areas from the one or more candidate care areas based on the boundary exposure parameters.

4. The system of claim 3, wherein the one or more exposure parameters comprise:
at least one of an exposed dose of illumination, a wavelength of illumination, a focal volume of the selected lithography tool during exposure or a spatial distribution of illumination on the sample during exposure.

5. The system of claim 2, wherein selecting one or more care areas from the one or more candidate care areas for mitigation further comprises:
directing the fabrication tool to fabricate the one or more candidate care areas on one or more test samples according to the production recipe;
directing a metrology tool to inspect the one or more candidate care areas on the one or more test samples to generate one or more measured stochastic repeaters; and
selecting the one or more care areas from the one or more candidate care areas based on the one or more measured stochastic repeaters.

6. The system of claim 1, wherein selecting one or more care areas from the one or more candidate care areas for mitigation comprises:
   directing the fabrication tool to fabricate the one or more candidate care areas on one or more test samples according to the production recipe;
   directing a metrology tool to inspect the one or more care areas of the one or more test samples to generate one or more measured stochastic repeaters; and
   selecting the one or more care areas from the one or more candidate care areas based on the one or more measured stochastic repeaters.

7. The system of claim 6, wherein selecting one or more care areas from the one or more candidate care areas for mitigation further comprises:
   directing the fabrication tool to fabricate the one or more candidate care areas on the one or more test samples with variations of the one or more exposure parameters from the production recipe to determine boundary exposure parameters for the one or more measured stochastic repeaters;
   directing the metrology tool to inspect the one or more care areas on the one or more test samples to determine boundary exposure parameters for the one or more measured stochastic repeaters; and
   selecting the one or more care areas from the one or more candidate care areas based on the boundary exposure parameters.

8. The system of claim 7, wherein the one or more exposure parameters comprise:
   at least one of an exposed dose of illumination, a wavelength of illumination, a focal volume of the selected lithography tool during exposure or a spatial distribution of illumination on the sample during exposure.

9. The system of claim 1, wherein selecting one or more care areas from the one or more candidate care areas for mitigation comprises:
   selecting the one or more care areas based a comparison of the one or more candidate care areas to a library of pattern layouts having known predicted likelihoods of stochastic repeaters.

10. The system of claim 9, wherein selecting the one or more care areas based a comparison of the one or more candidate care areas to a library of pattern layouts having known predicted likelihoods of stochastic repeaters comprises:
    selecting the one or more care areas based a comparison of the one or more candidate care areas to the library of pattern layouts having predicted likelihoods of stochastic repeaters using at least one of a deep learning technique or a neural network technique.

11. The system of claim 1, wherein the one or more exposure parameters comprise:
    at least one of an exposed dose of illumination, a wavelength of illumination, a focal volume of the selected lithography tool during exposure or a spatial distribution of illumination on the sample during exposure.

12. The system of claim 1, wherein selecting one or more care areas from the one or more candidate care areas for mitigation comprises:
    ranking predicted defect likelihoods of the one or more stochastic repeaters in the one or more candidate care areas, wherein modifying the production recipe to mitigate the one or more stochastic repeaters within the one or more care areas comprises:
    modifying the production recipe to mitigate a subset of the stochastic repeaters having predicted defect likelihoods greater than a selected threshold based on the ranking.

13. The system of claim 1, wherein modifying the production recipe to mitigate the stochastic repeaters within the one or more care areas comprises:
    modifying at least one exposure parameter of the one or more exposure parameters.

14. The system of claim 1, wherein modifying the production recipe to mitigate the stochastic repeaters within the one or more care areas comprises:
    modifying the pattern of elements based on optical proximity correction.

15. The system of claim 14, wherein modifying the additional pattern of elements based on optical proximity correction comprises:
    modifying at least one of a size or a position of at least one sub-resolution assist feature of the pattern of elements.

16. The system of claim 1, wherein the production recipe further comprises:
    one or more properties of a photoresist layer on the sample.

17. The system of claim 16, wherein the one or more properties of a photoresist layer on the sample comprise:
    at least one of a size of one or more polymer chains in the photoresist layer or a concentration of a photoacid generator in the photoresist layer.

18. The system of claim 1, further comprising:
    generating a metrology recipe of a metrology tool to monitor the one or more care areas; and
    inspecting the one or more care areas on the at least one sample fabricated according to the modified production recipe.

19. The system of claim 1, wherein identifying one or more candidate care areas including portions of the pattern of elements susceptible to stochastic repeaters by analyzing uncertainty of energy absorption in the sample and sensitivity of the pattern of elements to variations in absorbed energy comprises:
    estimating edge roughness of at least a portion of the pattern of elements by analyzing uncertainty of energy absorption near one or more edges in the pattern of elements and a sensitivity of the one or more edges to variations in absorbed energy.

20. A method comprising:
    receiving a production recipe including at least a pattern of elements to be fabricated on a sample using a selected lithography tool and one or more exposure parameters for exposing the pattern of elements during fabrication;
    identifying one or more candidate care areas including portions of the pattern of elements susceptible to stochastic repeaters by analyzing uncertainty of energy absorption in the sample and sensitivity of the pattern of elements to variations in absorbed energy, the stochastic repeaters including one or more portions of the pattern of elements predicted to exhibit stochastic fabrication errors;
    selecting one or more care areas from the one or more candidate care areas for mitigation based on predicted likelihoods of the stochastic repeaters in the one or more care areas when fabricated according to the production recipe using the selected lithography tool;
    modifying the production recipe to mitigate the stochastic repeaters within the one or more care areas; and fabricating at least one sample according to the modified production recipe.

21. The method of claim 20, wherein the one or more exposure parameters comprise:
at least one of an exposed dose of illumination, a wavelength of illumination, a focal volume of the selected lithography tool during exposure or a spatial distribution of illumination on the sample during exposure.

22. The method of claim 20, wherein modifying the production recipe to mitigate the stochastic repeaters within the one or more care areas comprises:
modifying at least one exposure parameter of the one or more exposure parameters.

23. The method of claim 20, wherein modifying the production recipe to mitigate the stochastic repeaters within the one or more care areas comprises:
modifying the pattern of elements based on optical proximity correction.

24. The method of claim 23, wherein modifying the pattern of elements based on optical proximity correction comprises:
modifying at least one of a size or a position of at least one sub-resolution assist feature of the pattern of elements.

25. The method of claim 20, wherein the production recipe further comprises:
one or more properties of a photoresist layer on the sample.

26. The method of claim 25, wherein the one or more properties of a photoresist layer on the sample comprise:
at least one of a size of one or more polymer chains in the photoresist layer or a concentration of a photoacid generator in the photoresist layer.

27. The method of claim 20, further comprising:
generating a metrology recipe of a metrology tool to monitor the one or more care areas of the additional pattern of elements; and
inspecting the one or more care areas on the at least one sample fabricated according to the modified production recipe.

28. A system comprising:
a controller configured to communicatively couple to a metrology tool and a fabrication tool, the controller including one or more processors configured to execute program instructions causing the one or more processors to:
receive a production recipe including at least a pattern of elements to be fabricated on a sample using a selected lithography tool and one or more exposure parameters for exposing the pattern of elements during fabrication;
identify one or more candidate care areas including portions of the pattern of elements susceptible to stochastic repeaters by analyzing uncertainty of energy absorption in the sample and sensitivity of the pattern of elements to variations in absorbed energy, the stochastic repeaters including one or more portions of the pattern of elements predicted to exhibit stochastic fabrication errors;
select one or more care areas from the one or more candidate care areas for mitigation based on predicted likelihoods of the stochastic repeaters in the one or more care areas when fabricated according to the production recipe using the selected lithography tool;
direct the fabrication tool to fabricate at least one sample according to the production recipe;
generate a metrology recipe of the metrology tool to monitor the one or more care areas; and
direct the metrology tool to inspect the one or more care areas on the at least one sample.

29. The system of claim 28, wherein generating the metrology recipe comprises:
determining at least one of an inspection sensitivity or a number of inspection measurements for inspecting the one or more care areas.

30. The system of claim 28, wherein generating a metrology recipe comprises:
determining a sampling plan including locations of at least some of the one or more care areas on the sample.

31. The system of claim 30, wherein the sampling plan includes locations of a subset of the one or more care areas on the sample.

32. The system of claim 28, wherein generate a metrology recipe of the metrology tool to monitor the one or more care areas comprises:
generate the metrology recipe of the metrology tool to monitor the one or more care areas on at least one of a wafer or a reticle.

33. A method comprising:
receiving a production recipe including at least a pattern of elements to be fabricated on a sample using a selected lithography tool and one or more exposure parameters for exposing the pattern of elements during fabrication;
identifying one or more candidate care areas including portions of the pattern of elements susceptible to stochastic repeaters by analyzing uncertainty of energy absorption in the sample and sensitivity of the pattern of elements to variations in absorbed energy, the stochastic repeaters including one or more portions of the pattern of elements predicted to exhibit stochastic fabrication errors;
selecting one or more care areas from the one or more candidate care areas for mitigation based on predicted likelihoods of the stochastic repeaters in the one or more care areas when fabricated according to the production recipe using the selected lithography tool;
fabricating at least one sample according to the production recipe;
generating a metrology recipe of a metrology tool to monitor the one or more care areas; and
inspecting the one or more care areas on the at least one sample.

34. The method of claim 33, wherein generating the metrology recipe comprises:
determining at least one of an inspection sensitivity or a number of inspection measurements for inspecting the one or more care areas.

35. The method of claim 33, wherein generating a metrology recipe comprises:
determining a sampling plan including locations of at least some of the one or more care areas on the sample.

36. The method of claim 35, wherein the sampling plan includes locations of a subset of the one or more care areas on the sample.

* * * * *